US011743631B2

(12) United States Patent
Kim et al.

(10) Patent No.: US 11,743,631 B2
(45) Date of Patent: Aug. 29, 2023

(54) SEAMLESS LISTEN-THROUGH BASED ON AUDIO ZOOM FOR A WEARABLE DEVICE

(71) Applicant: QUALCOMM Incorporated, San Diego, CA (US)

(72) Inventors: Lae-Hoon Kim, San Diego, CA (US); Dongmei Wang, Bellevue, WA (US); Fatemeh Saki, San Diego, CA (US); Taher Shahbazi Mirzahasanloo, San Diego, CA (US); Erik Visser, San Diego, CA (US); Rogerio Guedes Alves, Macomb Township, MI (US)

(73) Assignee: Qualcomm Incorporation, San Diego, CA (US)

( * ) Notice: Subject to any disclaimer, the term of this patent is extended or adjusted under 35 U.S.C. 154(b) by 0 days.

(21) Appl. No.: 18/063,493

(22) Filed: Dec. 8, 2022

(65) Prior Publication Data

US 2023/0105655 A1 Apr. 6, 2023

Related U.S. Application Data

(63) Continuation of application No. 17/201,998, filed on Mar. 15, 2021, now Pat. No. 11,589,153, which is a continuation of application No. 16/896,010, filed on Jun. 8, 2020, now Pat. No. 10,951,975, which is a continuation of application No. 16/285,923, filed on Feb. 26, 2019, now Pat. No. 10,681,452.

(51) Int. Cl.

| | |
|---|---|
| ***H03B 29/00*** | (2006.01) |
| ***A61F 11/06*** | (2006.01) |
| ***G10K 11/16*** | (2006.01) |
| ***H04R 1/10*** | (2006.01) |

(52) U.S. Cl.
CPC ......... *H04R 1/1083* (2013.01); *H04R 1/1075* (2013.01); *H04R 2420/07* (2013.01); *H04R 2460/01* (2013.01); *H04R 2460/13* (2013.01)

(58) Field of Classification Search
CPC ............................ H04R 1/1083; H04R 1/1075
See application file for complete search history.

(56) References Cited

U.S. PATENT DOCUMENTS

| | | | | |
|---|---|---|---|---|
| 9,401,158 | B1 | 7/2016 | Yen et al. | |
| 10,034,092 | B1 * | 7/2018 | Nawfal | H04R 5/027 |
| 10,681,452 | B1 | 6/2020 | Kim | |
| 10,951,975 | B2 | 3/2021 | Kim et al. | |

(Continued)

*Primary Examiner* — Simon King
(74) *Attorney, Agent, or Firm* — Espartaco Diaz Hidaglo

(57) ABSTRACT

A wearable device may include a processor configured to perform active noise cancelation (ANC) applied to an input audio signal received by at least one microphone, and detect a self-voice signal, based on one or more transducers. The processor may also be configured to apply a first filter to an external audio signal, detected by at least one external microphone on the wearable device, during a listen through operation based on an activation of the audio zoom feature to generate a first listen-through signal that includes the external audio signal. The processor may also be configured to after the activation of the audio zoom feature terminate a second filter that provides low frequency compensation. The processor may be configured to produce an output audio signal that is based on at least the first listen-through signal that includes the external signal, and is based on the detected self-voice signal.

28 Claims, 10 Drawing Sheets

(56) References Cited

U.S. PATENT DOCUMENTS

| | | | |
|---|---|---|---|
| 2007/0038457 | A1 | 2/2007 | Hwang et al. |
| 2010/0119077 | A1 | 5/2010 | Platz et al. |
| 2010/0131269 | A1 | 5/2010 | Park et al. |
| 2011/0007907 | A1 | 1/2011 | Park et al. |
| 2011/0135120 | A1 | 6/2011 | Larsen et al. |
| 2011/0288860 | A1 | 11/2011 | Schevciw et al. |
| 2013/0287219 | A1 | 10/2013 | Hendrix et al. |
| 2014/0126736 | A1 | 5/2014 | Gauger, Jr. et al. |
| 2015/0043762 | A1 | 2/2015 | Kim et al. |
| 2015/0271602 | A1 | 9/2015 | Gauger, Jr. |
| 2017/0103775 | A1 | 4/2017 | Xu |
| 2017/0193974 | A1 | 7/2017 | Gadonniex et al. |
| 2017/0193978 | A1 | 7/2017 | Goldman |
| 2017/0365245 | A1* | 12/2017 | Ku .................. G10K 11/17854 |
| 2018/0033447 | A1 | 2/2018 | Ramprashad et al. |
| 2018/0047410 | A1 | 2/2018 | Von et al. |
| 2018/0114518 | A1 | 4/2018 | Scanlan |
| 2018/0115839 | A1 | 4/2018 | Eichfeld et al. |
| 2018/0167715 | A1 | 6/2018 | Graylin et al. |
| 2018/0262849 | A1 | 9/2018 | Farmani et al. |
| 2019/0043518 | A1 | 2/2019 | Li |
| 2019/0214036 | A1 | 7/2019 | Wurtz et al. |
| 2020/0020313 | A1* | 1/2020 | Hua .................... H04R 1/1016 |
| 2020/0258493 | A1* | 8/2020 | Gauger, Jr. ...... G10K 11/17853 |
| 2021/0204053 | A1 | 7/2021 | Kim et al. |

* cited by examiner

SEAMLESS LISTEN-THROUGH BASED ON AUDIO ZOOM FOR A WEARABLE DEVICE

CROSS-REFERENCE TO RELATED APPLICATIONS

This application claims the benefit of Continuation application Ser. No. 17/201,998, filed Mar. 15, 2021 "Seamless Listen-Through For A Wearable Device", which claims benefit of Continuation application Ser. No. 16/896,010, filed Jun. 8, 2020, entitled "Seamless Listen-Through For A Wearable Device" which claims benefit of Non-Provisional application Ser. No. 16/285,923, filed Feb. 26, 2019, entitled "Seamless Listen-Through For A Wearable Device" which is incorporated herein by reference in its entirety.

BACKGROUND

The following relates generally to signal processing, and more specifically to seamless listen-through for a wearable device.

A user may use a wearable device and may wish to experience a listen-through feature. In some examples, when a user speaks (e.g., generates a self-voice signal), the user's voice may travel along two paths: an acoustic path and a bone conduction path. However, distortion patterns from external or background signals may be different than distortion patterns created by self-voice signals. Microphones picking up an input audio signal (e.g., including background noise and self-voice signals) may not seamlessly deal with the different types of signals. The different distortion patterns for different signals may result in a lack of natural sounding audio input when using a listen-through feature on the wearable device.

SUMMARY

The described techniques relate to improved methods, systems, devices, and apparatuses that support seamless listen-through for a wearable device. Generally, as provided for by the described techniques, a wearable device may store, in a memory, a self-voice signal via one or more transducers. The wearable device, may be coupled to the memory and be configured to perform active noise cancelation (ANC) applied to an input audio signal received by at least one microphone and detect the self-voice signal, based on the one or more transducers. The processor may be configured to apply a first filter to an external audio signal, detected by at least one external microphone on the wearable device, during a listen through operation based on an activation of the audio zoom feature to generate a first listen-through signal that includes the external audio signal. The processor may also be configured to after the activation of the audio zoom feature terminate a second filter that provides low frequency compensation. Moreover, the processor may be configured to produce an output audio signal that is based on at least the first listen-through signal that includes the external signal, and is based on the detected self-voice signal.

DETAILED DESCRIPTION

Figure 1:
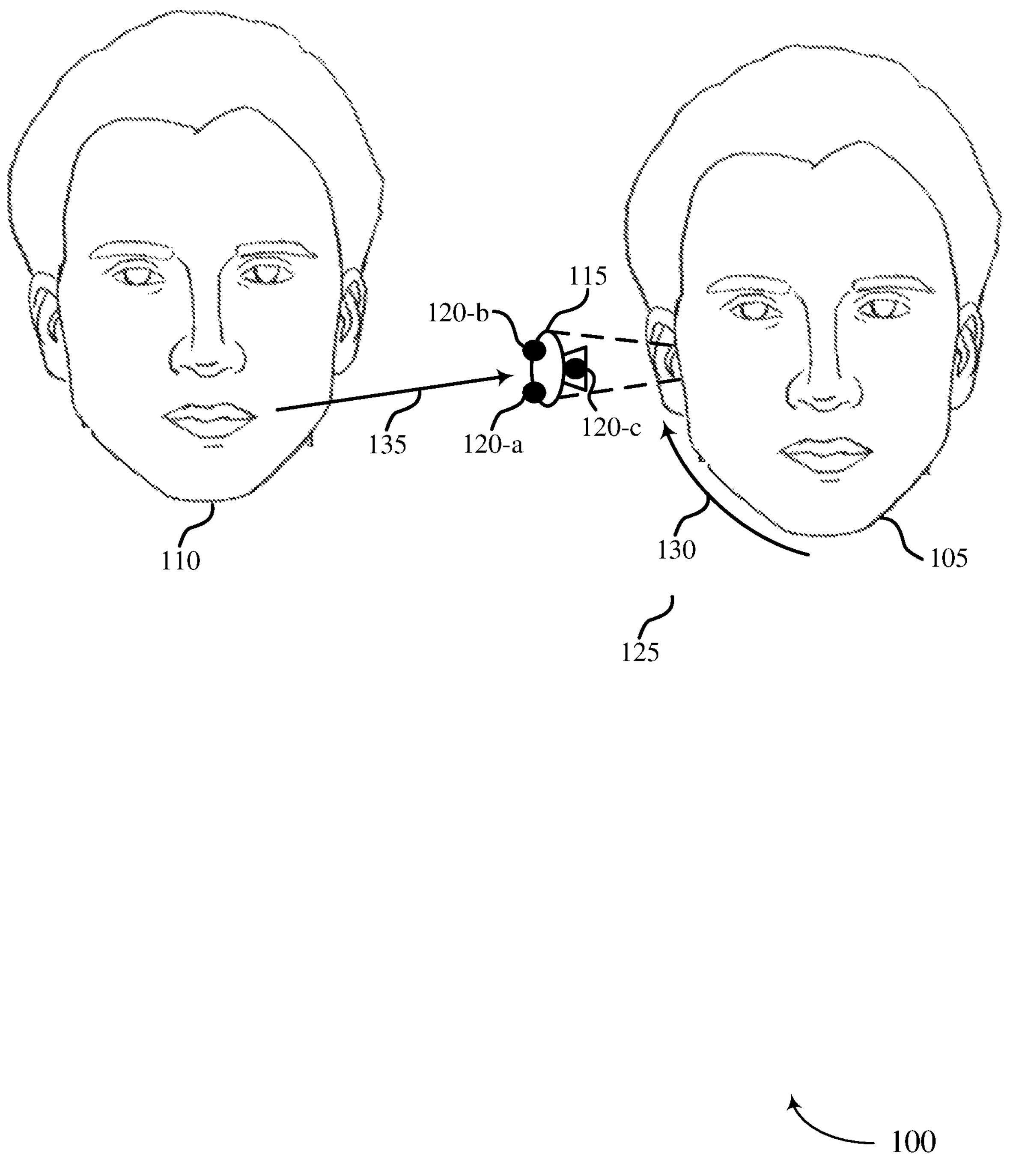
FIG. 1 illustrates an example of an audio signaling scenario that supports seamless listen-through for a wearable device in accordance with aspects of the present disclosure.

Some users may utilize a wearable device (e.g., a wireless communication device, wireless headset, earbud, speaker, hearing assistance device, or the like), and may wear the device to make use of it in a hands-free manner. Some wearable devices may include multiple microphones attached on the outside and inside of the device. These microphones may be used for multiple purposes, such as noise detection, audio signal output, active noise cancellation, and the like. When the user (e.g., wearer) of the wearable device speaks, they may generate a unique audio signal (e.g., self-voice). For example, the user's self-voice signal may travel along an acoustic path (e.g., from the user's mouth to the microphones of the headset) and along a second sound path created by vibrations via bone conduction between the user's mouth and the microphones of the headset. In some examples, a wearable device may perform self-voice activity detection (SVAD) based on the self-voice qualities. For instance, inter channel phase and intensity differences (e.g., interaction between the external microphones and the internal microphones of the wearable device) may be used as qualifying features to discriminate between self-speech signals and external signals. Upon detecting such differences (e.g., performing SVAD), the wearable device may determine when self-voice is present in an input audio signal.

In some examples, a wearable device may provide a listen-through feature. A listen-through feature may allow the user to hear, through the device, as if the device were not present. Such examples of listen-through features may allow a user to wear the wearable device in a hands-free manner (allowing the user to perform other tasks or go about their business) regardless of a current use-case of the wearable device (e.g., regardless of whether the device is currently in use). A listen-through feature may utilize both outer and inner microphones of the wearable device to receive an input audio signal, process the input audio signal, and output an output audio signal that sounds natural to the user (e.g., sounds as if the user were not wearing a device).

Self-voice signals and external signals may have different distortion patterns. This may occur because of the acoustic and bone conduction paths of a self-voice signal, while background and other external noise may simply follow acoustic paths. Because of the different distortion patterns, when the microphones of the wearable headset pick up self-voice signals and external signals without any discrimination, the user may not experience a natural sounding input audio signal.

In some examples, the wearable headset may apply separate filters (e.g., sinusoidal transient modeling (STM) filters to self-voice signals and external signals. The wearable device may receive an input audio signal (e.g., including both an external signal and a self-voice signal). In some examples, the wearable device may detect the self-voice signal in the input audio signal based on an SVAD procedure and may implement the described techniques based thereon. The wearable device may perform beamforming operations or other separation algorithms. For instance, the beamforming procedure may be based on a location of the microphones of the wearable device, the spacing of the microphones, the orientation of the microphones, or the like. For instance, the wearable device may apply a multi-mic generative network (MSGN) procedure, or a generalized eigenvalue beamforming procedure, or a beamforming procedure, or the like. The wearable device may isolate the external signal and the self-voice signal from the input audio signal, based on the separation procedure (e.g., beamforming). The wearable device may apply a first filter to the external signal, and a second filter to the self-voice signal. The wearable device may then mix the filtered signals and generate an output signal that sounds natural to the user.

Aspects of the disclosure are initially described in the context of a signal processing system. Aspects of the disclosure are further illustrated by and described with reference to signal processing schemes and audio signaling scenarios. Aspects of the disclosure are further illustrated by and described with reference to apparatus diagrams, system diagrams, and flowcharts that relate to seamless listen-through for a wearable device.

FIG. 1 illustrates an example of an audio signaling scenario 100 that supports seamless listen-through for a wearable device in accordance with aspects of the present disclosure. Audio signaling scenario 100 may occur when a user 105 using a wearable device 115 desires to experience a listen-through feature.

A user 105 may use a wearable device 115 (e.g., a wireless communication device, wireless headset, ear-bud, speaker, hearing assistance device, or the like), which may be worn by user 105 in a hands-free manner. In some cases, the wearable device 115 may also be referred to as a hearable device. In some examples, user 105 may desire to continuously wear wearable device 115, whether wearable device 115 is currently in use or not. In some examples, wearable device 115 may include multiple microphones 120. For instance, wearable device 115 may include one or more outer microphones, such as microphone 120-*a* and 120-*b*. Wearable device 115 may also include one or more inner microphones, such as inner microphone 120-*c*. Wearable device 115 may use microphones 120 for noise detection, audio signal output, active noise cancellation, and the like. When user 105 speaks, user 105 may generate a unique audio signal (e.g., self-voice). For example, user 105 may generate a self-voice signal that may travel along an acoustic path 125 (e.g., from the mouth of user 105 to the microphones 120 of the headset). User 105 may also generate a self-voice signal that may follow a sound conduction path 130 created by vibrations via bone conduction between the user's mouth and the microphones 120 of wearable device 115. In some examples, a wearable device 115 may perform self-voice activity detection (SVAD) based on the self-voice qualities. For instance, wearable device 115 may identify inter channel phase and intensity differences (e.g., interaction between the external microphones 120-*a* and 120-*b* and the internal microphones 120-*c* of the wearable device 115). Wearable device 115 may use the detected differences as qualifying features to discriminate between self-speech signals and external signals. For instance, if the differences between channel phase and intensity between inner microphone 120-*c* and outer microphone 120-*a* are detected at all, or if differences between channel phase and intensity between inner microphone 120-*c* and outer microphone-a satisfy a threshold value, then wearable device 115 may determine that a self-voice signal is present in an input audio signal.

In some examples, wearable device 115 may provide a listen-through feature. A listen-through feature may allow user 105 to hear, through the wearable device 115, as if the wearable device 115 were not present. The listen-through feature may allow user 105 to wear the wearable device 115 in a hands-free manner (allowing the user to perform other tasks or go about their business) regardless of current use-case of the wearable device (e.g., regardless of whether the device is currently in use). For instance, an audio source 110 (e.g., another person) may generate an external noise 135 (e.g., the other person may speak to user 105). Without a listen-through feature, external noise 135 may be blocked, muffled, or otherwise distorted by wearable device 115. A listen-through feature may utilize both outer microphones 120-*a* and 120-*b*, and inner microphones 120-*c* of the wearable device to receive an input audio signal (e.g., external noise 135), process the input audio signal, and output an output audio signal (e.g., via inner microphone 120-*c*) that sounds natural to user 105 (e.g., sounds as if the user were not wearing a device).

Self-voice signals and external signals may have different distortion patterns. For instance, external noise 135 and/or self-voice following acoustic path 125 may have a first distortion pattern. But self-voice following conduction path 130 and/or a combination of self-voice following acoustic path 125 in combination with self-voice following conduction path 130 may have a second distortion pattern. Microphones 120 of wearable device 115 may detect self-voice signals and external signals without any discrimination. Thus, without different treatments for the different signal types, user 105 may not experience a natural sounding input audio signal. That is, wearable device 115 may detect an input audio signal including a combination of external noise 135, and self-voice via acoustic path 125 and conduction path 130. Wearable device 115 may detect the input audio signal using microphones 120. In some examples, wearable device 115 may detect the external noise 135 and self-voice via acoustic path 125 with outer microphones 120-*a* and 120-*b*. In some examples, wearable device 115 may detect self-voice via conduction path 130 with one or more inner microphones 120-*c*. Wearable device 115 may apply the same filtering procedure to all of the received signals and generates an output audio signal which it relays to user 105 (e.g., via inner microphone 120-*c*). In such examples, the combined output audio signal may not sound natural, due to the different distortion patterns.

In some examples, to achieve natural sounding output audio signals (e.g., a successful listen-through feature), wearable device 115 may apply separate STM filters to self-voice signals and external signals. Wearable device 115 may receive an input audio signal (e.g., including external noise 135, and self-voice via acoustic path 125 and conduction path 130). In some examples, wearable device 115 may detect the self-voice signal in the input audio signal based on an SVAD procedure and may implement the described techniques based thereon. Wearable device 115 may perform beamforming operations or other separation algorithms. Beamforming may be performed as described in greater detail with respect to FIG. 3. For instance, the beamforming procedure may be based on a location of the microphones 120 of the wearable device 115, the spacing of the microphones 120, the orientation of the microphones 120, or the like. Such characteristics of an array of microphones 120 may be used to perform constructive interference in a targeted direction, and destructive interference in all non-targeted directions. In some examples, wearable device 115 may perform other separation procedures, such as applying a multi-mic generative network (MSGN) procedure, or a generalized eigenvalue beamforming procedure, or a beamforming procedure, or the like. Wearable device 115 may isolate the external signal and the self-voice signal from the input audio signal, based on the separation procedure (e.g., beamforming). Wearable device 115 may apply a first filter to the external signal, and a second filter to the self-voice signal. Wearable device 115 may then mix the filtered signals and generate an output audio signal that sounds natural to user 105.

In some examples, user 105 may apply an audio zoom feature (e.g., may focus sound pickup in a desired direction). This may provide a zooming effect with the same stereo sensation to user 105 in the user 105 defined direction while the user wears the wearable device 115. A playback stereo output may be generated after beamforming toward the target direction. In some examples, wearable device 115 may suppress all sound outside of the target direction (e.g., including self-voice). Thus, wearable device 115 may remix the detected self-voice signals into the output audio signal. However, if all background noise is filtered and remixed into the output audio signal along with the self-voice, then the audio zoom feature may be rendered redundant. Thus, if wearable device 115 enables audio zoom, then a background noise path (e.g., a procedure for filtering and remixing background noise) may be cut off to achieve the audio zoom feature while separately filtering a self-voice signal.

Figure 2:
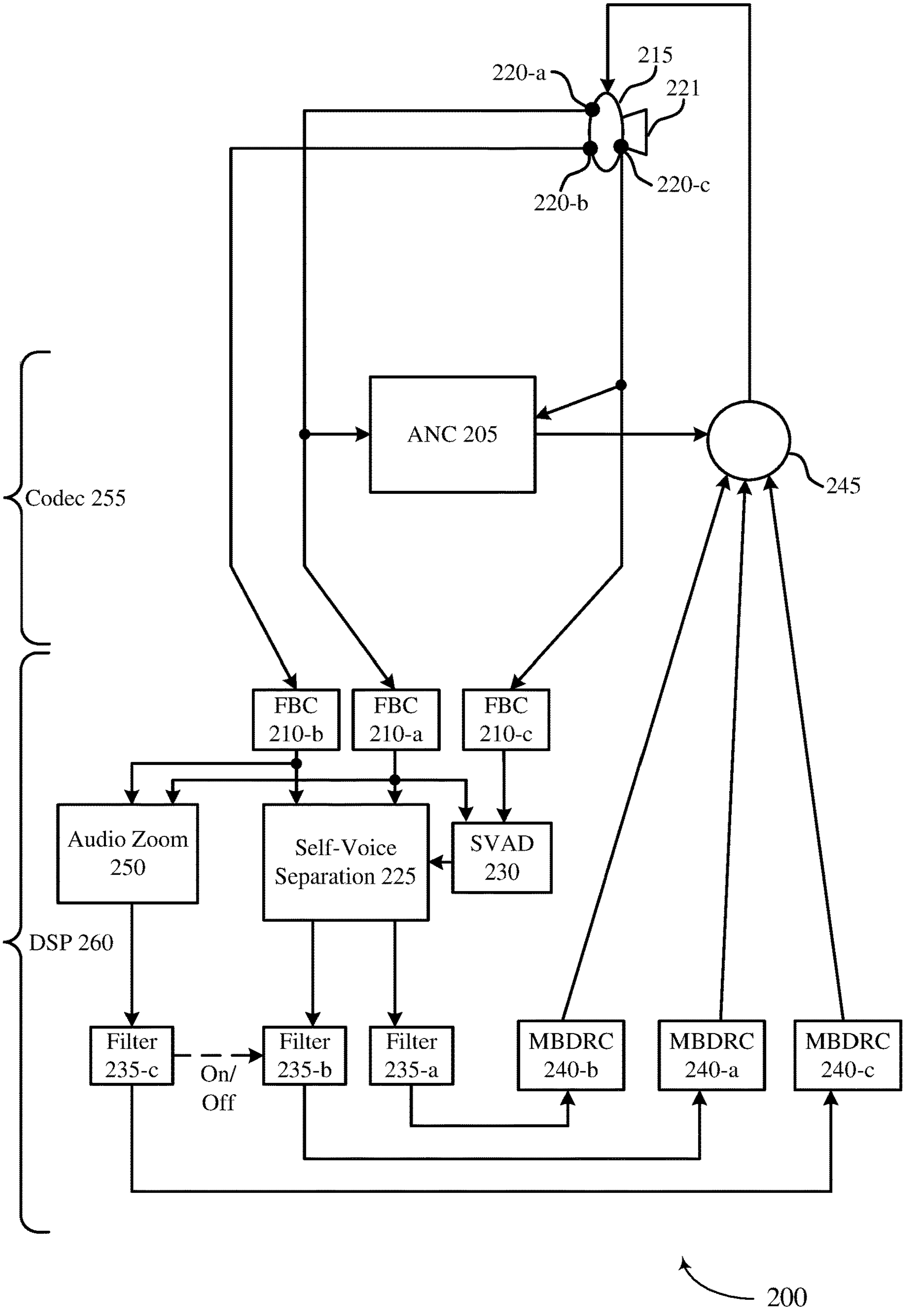
FIG. 2 illustrates an example of a signal processing scheme that supports seamless listen-through for a wearable device in accordance with aspects of the present disclosure.

FIG. 2 illustrates an example of a signal processing scheme 200 that supports seamless listen-through for a wearable device in accordance with aspects of the present disclosure. In some examples, signal processing scheme 200 may implement aspects of audio signaling scenario 100.

In some examples, wearable device 115 may detect an input audio signal. In a non-limiting illustrative example, inner microphone 220-*c* and outer microphone 220-*a* may primarily detect self-voice, and outer microphone 220-*b* may primarily detect external noise. For instance, inner microphone 220-*c* may detect at least a portion of a self-voice signal (e.g., may only detect a self-voice signal, or may detect a self-voice signal in combination with external signals). Inner microphone 220-*c* may detect a self-voice signal via a bone conduction path). Outer microphone 220-*a* (e.g., a right microphone of a two-microphone set, a microphone closest to a user's mouth, or a microphone oriented so as to more clearly receive self-voice via an acoustic path, or the like) may primarily detect a portion of a self-voice signal (e.g., may only detect a self-voice signal, or may detect a self-voice signal in combination with external signals). For instance, outer microphone 220-*a* may detect a self-voice signal via an acoustic path. Outer microphone 220-*a* may also detect all or part of an external signal (e.g., noise from another source that is not the user's voice). Outer microphone 220-*b* (e.g., a left microphone of a two-microphone set, a microphone farther from a user's mouth, or a microphone oriented so as to more clearly receive non-self-voice signals, or the like) may detect external noise (e.g., may only detect an external signal, or may detect a self-voice signal in combination with external signals). During a codec 255 portion of signal processing scheme 200, wearable device 215 may perform active noise cancelation (ANC) 205. ANC 205 may be particularly applied to the input audio signal received via outer microphone 220-*a* and inner microphone 220-*c* (e.g., which may include a self-voice signal). In some examples, ANC 205 may be applied to a final output audio signal at mixer 245.

During a digital signal processing (DSP) 260 portion of a signal processing scheme 200, wearable device 215 may, for example, apply feedback cancelation (FBC) 210-*a* for the input audio signal detected by outer microphone 220-*a*, may apply FBC 210-*b* for the input audio signal detected by outer microphone 220-*b*, and may apply FBC 210-*c* for the input audio signal detected by inner microphone 220-*c*.

Wearable device 115 may perform self-voice separation 225 on the input audio signal. Self-voice separation 225 may be based on a beam-forming procedure. For example, wearable device 115 may determine that an external signal is received more strongly by outer microphone 220-*b* based on the orientation, location, spacing, or the like, of outer microphone 220-*b*. Wearable device 215 may also determine that an acoustic portion of a self-voice is received more strongly by outer microphone 220-*a* based on similar parameters. Wearable device 215 may compare the received input audio signal at different microphones 220, and wearable device 215 may isolate the self-voice signal (e.g., detected by inner microphone 220-*c* and outer microphone 220-*a*) from the total input audio signal based thereon. That is, the total input audio signal minus the isolated self-voice signal may be equal to the external signal (e.g., background noise remaining after self-voice is removed from the input audio signal). In some examples, the self-voice separation 225 may be a multi-microphone speech generative network (MSGN) method, or a generalized eigenvalue (GEN) beamforming procedure, or a beamforming procedure, or the like. Some procedures (e.g., a GEN beamforming procedure) which may take advantage of an SVAD procedure. In some examples, in order to separate the self-voice signal from the external signal, wearable device 215 may detect a signal to interference ratio (SIR) that satisfies a threshold (e.g., 12 to 15 dBs). In some examples, Wearable device 115 may then apply separate filters 235 to the external signal and the self-voice signal based on self-voice separation 225.

In some examples, wearable device 215 may perform SVAD 230 on the input audio signal. SVAD 230 may include, for example, comparing one or more parameters (e.g., inter channel phase and intensity differences) of an input audio signal detected by inner microphone 220-*c* and outer microphone 220-*a*. If a difference between the parameters exists, or if a difference between the one or more parameters satisfies a threshold value, then SVAD 230 may identify the presence of a self-voice signal in the input audio signal. SVAD 230 may serve as a trigger for self-voice separation 225. For example, if SVAD 230 does not detect any self-voice, then wearable device 215 may have no self-voice separation 225 to perform. In some examples, SVAD 230 may trigger a switch between separate filters. For example, wearable device 215 may apply filter 235-*b* (e.g., a listen-through background (LT_B) filter) to an audio input signal. Filter 235-*b* may apply a high pass equalizer and a low-frequency compensation to the external signal. Filter 235-*a* (e.g., a listen-through self-voice (LT_S) filter or listen-through target (LT_T) filter) may be a filter for self-voice signals (e.g., detected by outer microphone 220-*a* and outer microphone 220-*b*). Filter 235-*a* may apply a high pass equalizer to compensate for high frequency loss. If SVAD 230 detects self-voice, it may trigger a switch. Wearable device 215 may perform self-voice separation 225, and switch from filter 235-*b* for external signals to filter 235-*a* for the isolated self-voice signal of the input audio signal. In some examples, the switching may result in a potential transition artifact. In some examples, wearable device 215 may continuously (e.g., simultaneously) apply different filters (e.g., filter 235-*b* and filter 235-*a*, respectively) to external signals and self-voice signals. In some examples, because of a masking effect, a playback target sound may dominate the external target sound reaching the ear drum. In some examples, an output audio signal may be equal to an audio input for a closed ear plus an audio input for an audio zoom portion of the signal plus active noise cancelation divided by an audio input on the closed ear plus the audio zoom portion of the signal. For example, an output audio signal may be calculated as shown in equation 1:

$$\frac{A_{closedEar+AZ+ANC}}{A_{closedEar+AZ}}$$

In some examples, wearable device 215 may apply an audio zoom 250 feature. Audio zoom 250 may use the multiple microphones 220 to apply beamforming in a target direction. In such examples, wearable device 215 may be able to provide the same stereo sensation (e.g., natural sounding listen-through features) in a targeted direction. Audio zoom 250 may suppress external signals that do not lie in the targeted direction, which may include the self-voice signal. In such examples, wearable device 215 may perform final processing to generate mixable audio streams (e.g., via multiband dynamic range compression (MBDRC) 240-*c*) and may remix filtered self-voice signals into an output audio signal at mixer 245. However, if audio zoom 250 has suppressed part or all of an external signal received by an outer microphone 220-*b*, then mixing in filtered external signals to the output audio signal may render audio zoom 250 redundant. That is, the purpose of audio zoom 250 may be to suppressed external signals (e.g., background noise) in a certain direction. If those external signals are separated from the input audio signal by self-voice separation 225 and filtered by filter 235-*b*, and then re-mixed into the output audio signal, then they may not be successfully suppressed, despite audio zoom 250. Thus, if wearable device 215 activates audio zoom 250 (e.g., a user manually activates the audio zoom feature or wearable device 215 detects a condition and automatically activates the audio zoom feature) then wearable device 215 may shut cut off the audio stream for external signals. For instance, wearable device may initiate filter 235-*c* (e.g., a listen-through audio zoom (LB_A) and terminate filter 235-*b*. Filter 235-*c* may include foreground sound processing and may include headphone or earphone equalization plus ANC compensation where ANC could suppress low frequency energy. Wearable device 215 may apply filter 235-*c* to the targeted external signal, process the filtered targeted external signal with MBDRC 240-*c* and mix the signals (e.g., the filtered targeted external signal and the filtered self-voice signal) with mixer 245 to generate an output audio signal. If wearable device 215 does not activate (or deactivates) audio zoom 250, then wearable device 215 may apply filter 235-*b* to external signals isolated by self-voice separation 225, process the filtered external signal with MBDRC 240-*b*, and mix the signals with mixer 245 to generate an output audio signal.

Upon mixing the various audio data streams at mixer 245, wearable device 215 may generate an output audio signal including the filtered and remixed self-voice signal and filtered and remixed external signal. In some examples, wearable device 215 may output the output audio signal via speaker 221, and the user may experience seamless listen-through based at least in part on the isolation and separate filtering of the self-voice signals and external signals.

Figure 3:
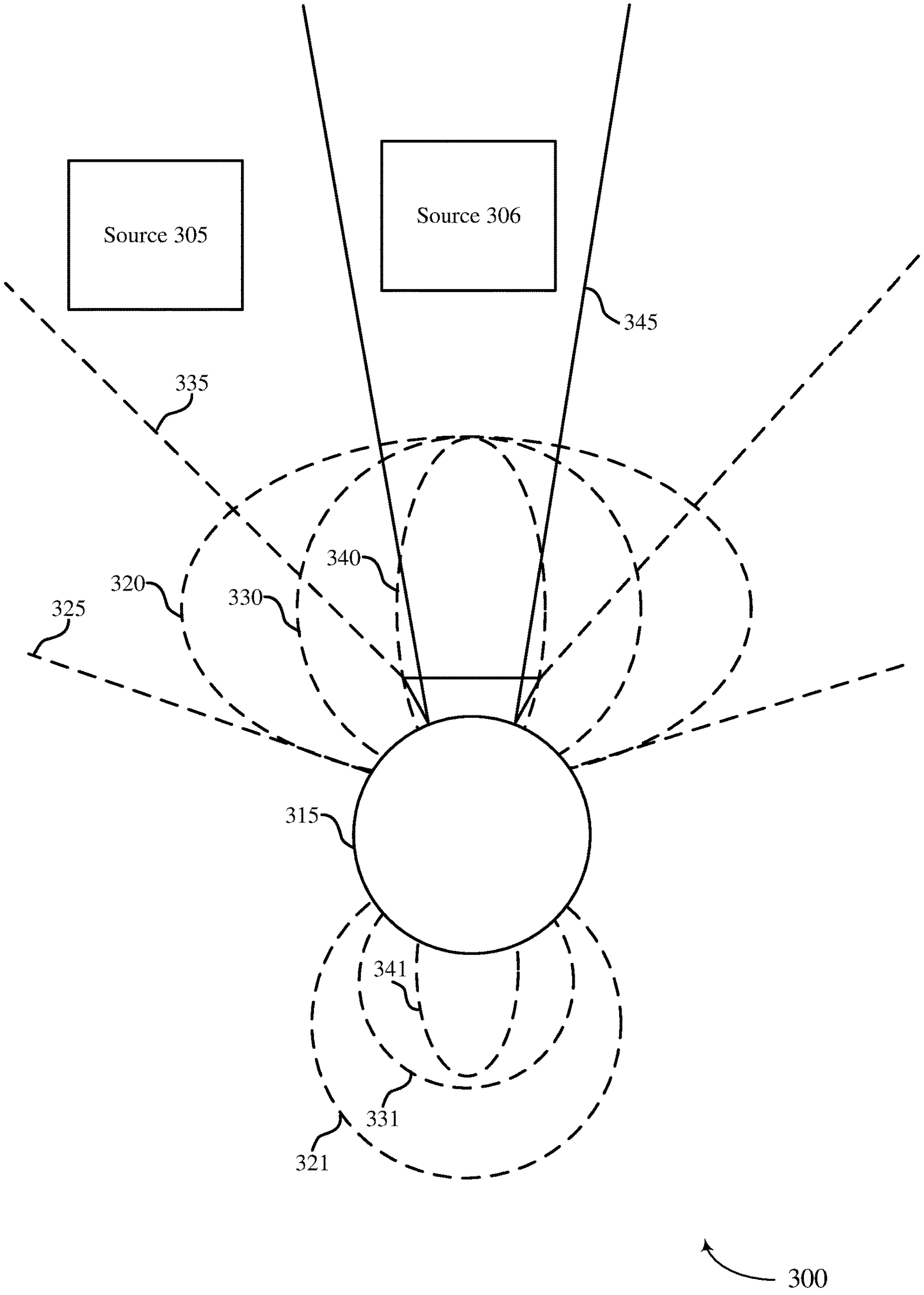
FIG. 3 illustrates an example of a beamforming scheme that supports seamless listen-through for a wearable device in accordance with aspects of the present disclosure.

FIG. 3 illustrates an example of a beamforming scheme 300 that supports seamless listen-through for a wearable device in accordance with aspects of the present disclosure. In some examples, beamforming scheme 300 may implement aspects of audio signaling scenario 100.

Wearable device 315 may perform an audio zoom function to receive an input audio signal from a targeted direction. Wearable device 315 may perform a beamforming operation (e.g., spatial filtering procedure). For example, one or more microphones (e.g., a microphone array) of wearable device 315 may be configured to form a receive beam. Wearable device 115 may configure or use spatial diversity of a set of microphones to detect or extract audio signals in a targeted direction and suppress background noise from non-targeted directions. This may be accomplished by identifying an interference pattern between the signals captured by the set of microphones. For instance, wearable device 215 may selectively combine received signals from respective microphones and utilizing constructive interference (e.g., for signals in the targeted direction) and destructive interference (e.g., for signals in the non-targeted direction). Thus, the set of microphones may act as a directed microphone.

In a non-limiting illustrative example, wearable device 315 may generate a receive beam 320 (which may create a node 321 in another direction). Beam 320 may allow wearable device 315 to receive targeted audio signals from a spatial range 325. Beam 320 may be relatively course. Wearable device 315 may generate a receive beam 330 (which may create a node 331 in another direction). Beam 330 may allow wearable device 315 to receive targeted audio signals from spatial range 335. Beam 330 may be less course than beam 320, and spatial range 335 may be more narrow than spatial range 325. Wearable device 315 may generate a receive beam 340 (which may create a node 341 in another direction). Beam 340 may allow wearable device 315 to receive targeted audio signals from spatial range 345. Beam 340 may be narrower than beam 320 or beam 330 and may be highly directional. Beam 330 may be broad enough to receive external signals from multiple sources (e.g., source 305 and source 306). Beam 340 may be highly directional to focus on a single source (e.g., source 306). For example, source 306 may be an individual with whom the user is conversing, and source 305 may be another person generating background noise. If wearable device 315 generates beam 340 for an audio zoom procedure, then wearable device 115 may suppress sound outside of spatial range 345 (including source 305) and may perform listen-through features on source 306 (and self-voice during the conversation). When wearable device 315 uses the described audio zoom feature, then wearable device 315 may shut off a processing flow for background device (e.g., to avoid remixing background noise from source 305 back into an output audio signal after performing the listen-through function on signals from source 306 and self-voice signals).

Figure 4:
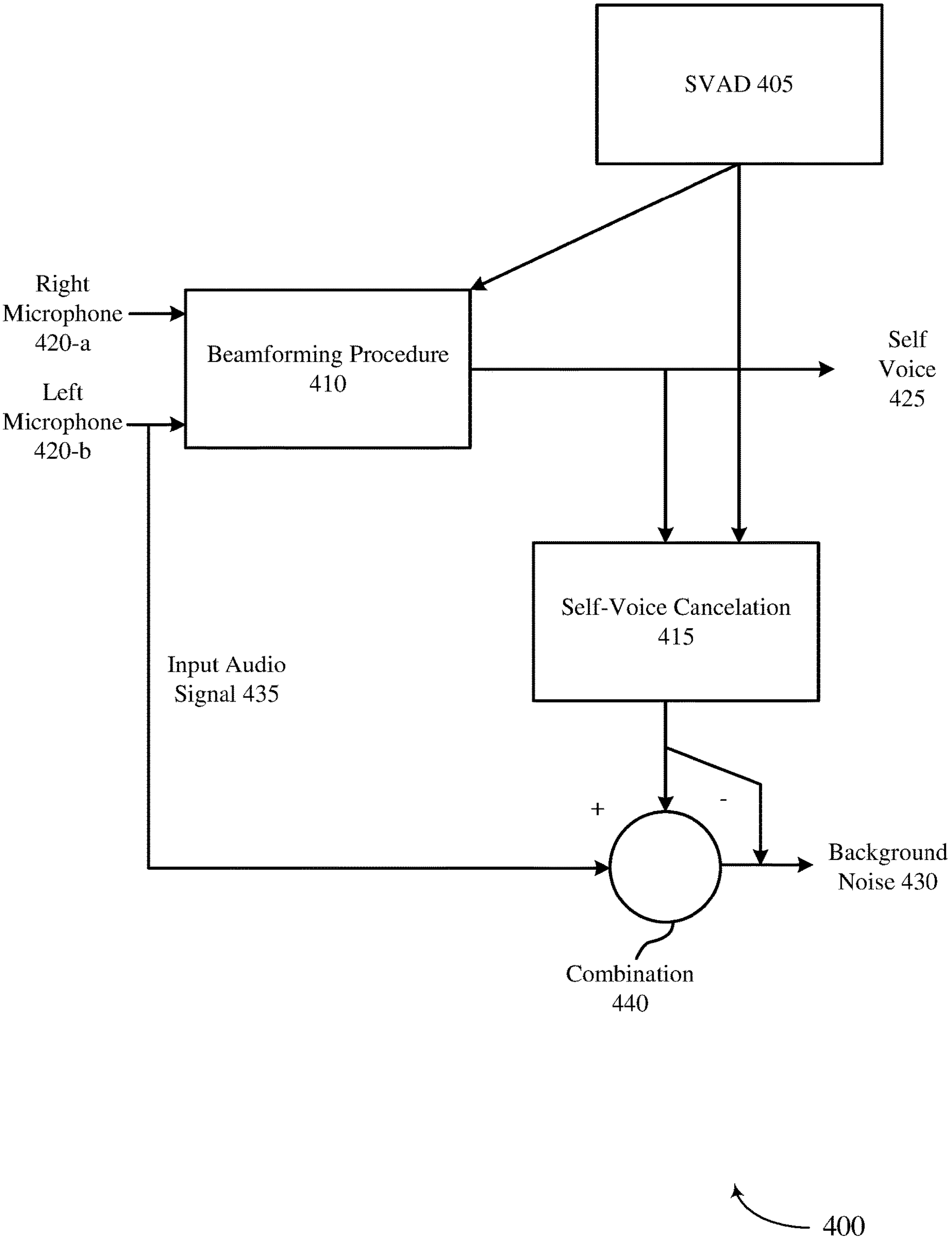
FIG. 4 illustrates an example of a signal processing scheme that supports seamless listen-through for a wearable device in accordance with aspects of the present disclosure.

FIG. 4 illustrates an example of a signal processing scheme 400 that supports seamless listen-through for a wearable device in accordance with aspects of the present disclosure. In some examples, signal processing scheme 400 may implement aspects of the audio signaling scenario 100 of FIG. 1.

A wearable device may perform signal processing on an input audio signal. For example, the wearable audio device may include multiple microphones, such as a right microphone 420-*a* and a left microphone 420-*b*. In some examples, SVAD 405 may identify the presence of self-voice signals. The wearable device may perform a beamforming procedure 410, which may isolate self-voice signals from external noise signals.

In some examples, SVAD 405 may trigger beamforming procedure 410. For instance, input audio signals may be received and processed without applying different filters. Upon detecting self-voice signals via SVAD 405, the wearable device may perform beamforming procedure 410 to isolate the self-voice signals. In some examples, SVAD 405 may continuously identify the presence or lack thereof of self-voice, and beamforming procedure 410 and separate filters may be continuously applied. In such examples, where SVAD 405 does not detect self-voice, then the value of self-voice 425 may be zero, and the background noise 430 may be equal to the input audio signal 435.

The wearable device may perform beamforming procedure 410 and may isolate a self-voice 425. Having isolated self-voice 425, the wearable device may perform self-voice cancelation 415. That is, the wearable device may cancel isolated self-voice 425 from input audio signal 435. Self-voice cancelation 415 may be applied to input audio signal 435 at combination 440, resulting in background noise 430. The wearable device may thus generate background noise 430 and self-voice 425 for separate filtering, as described in greater detail with respect to FIG. 2.

Figure 5:
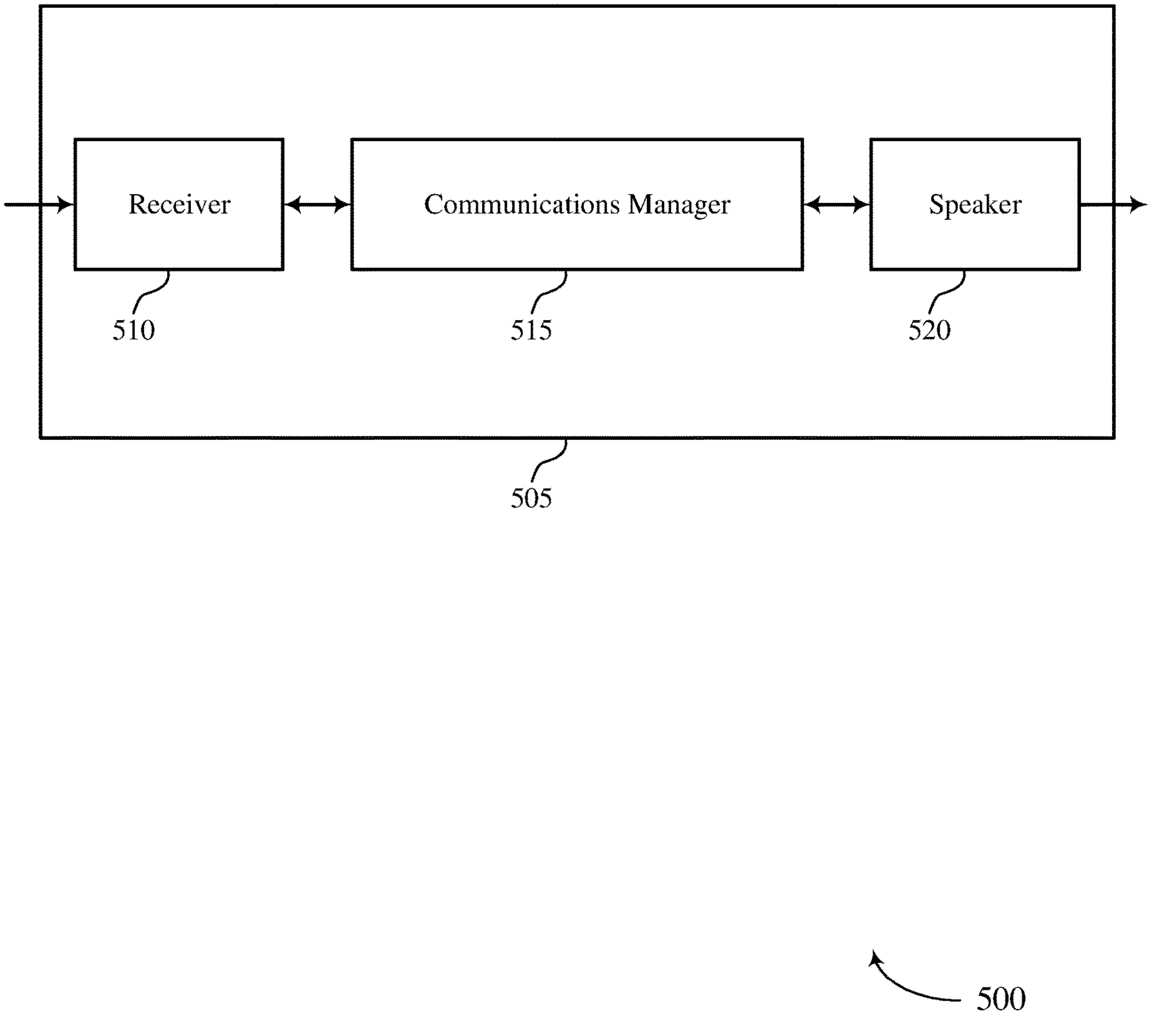
FIGS. 5 and 6 show block diagrams of wearable devices that support seamless listen-through for a wearable device in accordance with aspects of the present disclosure.

FIG. 5 shows a block diagram 500 of a wearable device 505 that supports seamless listen-through for the wearable device in accordance with aspects of the present disclosure. The wearable device 505 may be an example of aspects of a wearable device as described herein. The wearable device 505 may include a receiver 510, a signal processing manager 515, and a speaker 520. The wearable device 505 may also include a processor. Each of these components may be in communication with one another (e.g., via one or more buses).

The receiver 510 may receive audio signals from a surrounding area (e.g., via an array of microphones). Detected audio signals may be passed on to other components of the wearable device 505. The receiver 510 may utilize a single antenna or a set of antennas to communicate with other devices while providing seamless listen-through features.

The signal processing manager 515 may receive, at a wearable device including a set of microphones, an input audio signal, perform, based on the set of microphones, a beamforming operation, isolate, based on the beamforming operation, a self-voice signal and an external signal, apply a first filter to the external signal and a second filter to the self-voice signal, and output, to a speaker of the wearable device, an output audio signal based on a combination of the filtered external signal and the filtered self-voice signal. The signal processing manager 515 may be an example of aspects of the signal processing manager 810 described herein.

The signal processing manager 515, or its sub-components, may be implemented in hardware, code (e.g., software or firmware) executed by a processor, or any combination thereof. If implemented in code executed by a processor, the functions of the signal processing manager 515, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The signal processing manager 515, or its sub-components, may be physically located at various positions, including being distributed such that portions of functions are implemented at different physical locations by one or more physical components. In some examples, the signal processing manager 515, or its sub-components, may be a separate and distinct component in accordance with various aspects of the present disclosure. In some examples, signal processing manager 515, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The speaker 520 may provide output signals generated by other components of the wearable device 505. In some examples, the speaker 520 may be collocated with an inner microphone of wearable device 505. For example, the speaker 520 may be an example of aspects of the speaker 825 described with reference to FIG. 8.

Figure 6:
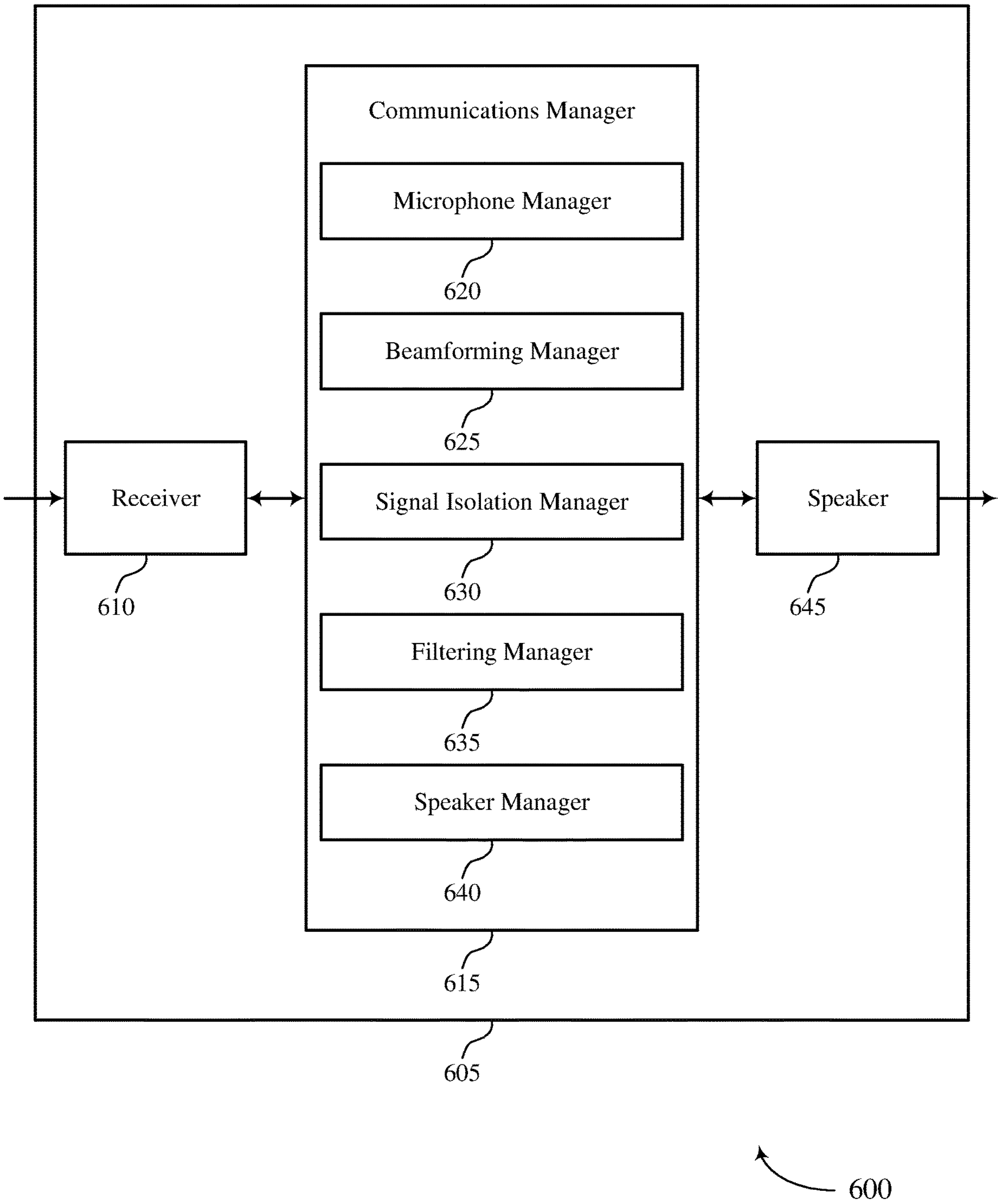

FIG. 6 shows a block diagram 600 of a wearable device 605 that supports seamless listen-through for a wearable device in accordance with aspects of the present disclosure. The wearable device 605 may be an example of aspects of a wearable device 505 or a wearable device 115, or 215 as described herein. The wearable device 605 may include a receiver 610, a signal processing manager 615, and a speaker 645. The wearable device 605 may also include a processor. Each of these components may be in communication with one another (e.g., via one or more buses).

The receiver 610 may receive audio signals (e.g., via a set of microphones). Information may be passed on to other components of the wearable device 605.

The signal processing manager 615 may be an example of aspects of the signal processing manager 515 as described herein. The signal processing manager 615 may include a microphone manager 620, a beamforming manager 625, a signal isolation manager 630, a filtering manager 635, and a speaker manager 640. The signal processing manager 615 may be an example of aspects of the signal processing manager 810 described herein.

The microphone manager 620 may receive, at a wearable device including a set of microphones, an input audio signal.

The beamforming manager 625 may perform, based on the set of microphones, a beamforming operation.

The signal isolation manager 630 may isolate, based on the beamforming operation, a self-voice signal and an external signal.

The filtering manager 635 may apply a first filter to the external signal and a second filter to the self-voice signal.

The speaker manager 640 may output, to a speaker of the wearable device, an output audio signal based on a combination of the filtered external signal and the filtered self-voice signal.

The speaker 645 may provide output signals generated by other components of the wearable device 605. In some examples, the speaker 645 may be collocated with a microphone. For example, speaker 645 may be an example of aspects of the speaker 825 described with reference to FIG. 8.

Figure 7:
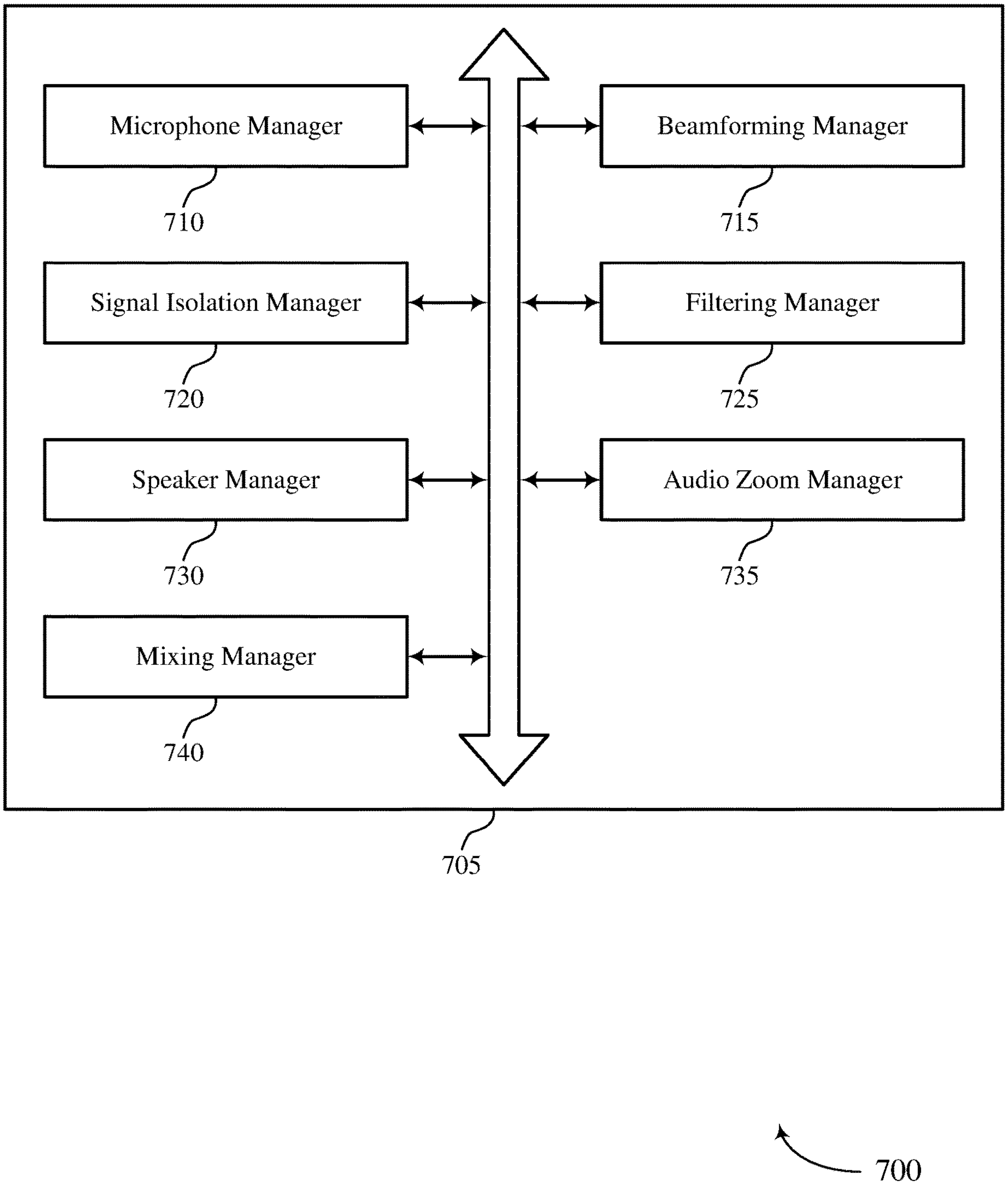
FIG. 7 shows a block diagram of a signal processing manager that supports seamless listen-through for a wearable device in accordance with aspects of the present disclosure.

FIG. 7 shows a block diagram 700 of a signal processing manager 705 that supports seamless listen-through for a wearable device in accordance with aspects of the present disclosure. The signal processing manager 705 may be an example of aspects of a signal processing manager 515, a signal processing manager 615, or a signal processing manager 810 described herein. The signal processing manager 705 may include a microphone manager 710, a beamforming manager 715, a signal isolation manager 720, a filtering manager 725, a speaker manager 730, an audio zoom manager 735, and a mixing manager 740. Each of these modules may communicate, directly or indirectly, with one another (e.g., via one or more buses).

The microphone manager 710 may receive, at a wearable device including a set of microphones, an input audio signal.

The beamforming manager 715 may perform, based on the set of microphones, a beamforming operation.

The signal isolation manager 720 may isolate, based on the beamforming operation, a self-voice signal and an external signal. In some examples, the signal isolation manager 720 may detect a presence of the self-voice signal, where performing the beamforming operation is based on the detecting. In some examples, the signal isolation manager 720 may isolate, based on the audio zoom procedure, a directional portion of the external signal.

The filtering manager 725 may apply a first filter to the external signal and a second filter to the self-voice signal. In some examples, the filtering manager 725 may configure a filter to perform a first filtering procedure on the external signal. In some examples, the filtering manager 725 may upon completion of the first filtering procedure, configuring the filter to perform a second filtering procedure on the self-voice signal. In some examples, the filtering manager 725 may simultaneously apply the first filter to the external signal and the second filter to the self-voice signal. In some examples, the filtering manager 725 may switch off a filtering procedure for background noise associated with the external signal.

In some examples, the filtering manager 725 may switch on a filtering procedure for background noise associated with the directional signal. In some examples, the filtering manager 725 may precompute a self-voice filter based on an orientation of the set of microphones, a location of the set of microphones, or a combination thereof. In some examples, the filtering manager 725 may detect a presence of the self-voice signal in the input audio signal. In some examples, the filtering manager 725 may set the second filter equal to the precomputed self-voice filter based on the detecting.

The speaker manager 730 may output, to a speaker of the wearable device, an output audio signal based on a combination of the filtered external signal and the filtered self-voice signal.

The audio zoom manager 735 may perform, based on the beamforming operation, an audio zoom procedure. In some examples, the audio zoom manager 735 may suppress, based on the audio zoom procedure, a remaining portion of the external signal.

The mixing manager 740 may identify, based on the first filter, one or more mixing parameters for the first signal. In some examples, the mixing manager 740 may identify, based on the second filter, one or more mixing parameters for the second signal. In some examples, the mixing manager 740 may mix the filtered external signal and the filtered self-voice signal according to the identified mixing parameters. In some cases, the mixing parameter may be a compensation value, an equalization value, or a combination thereof.

Figure 8:
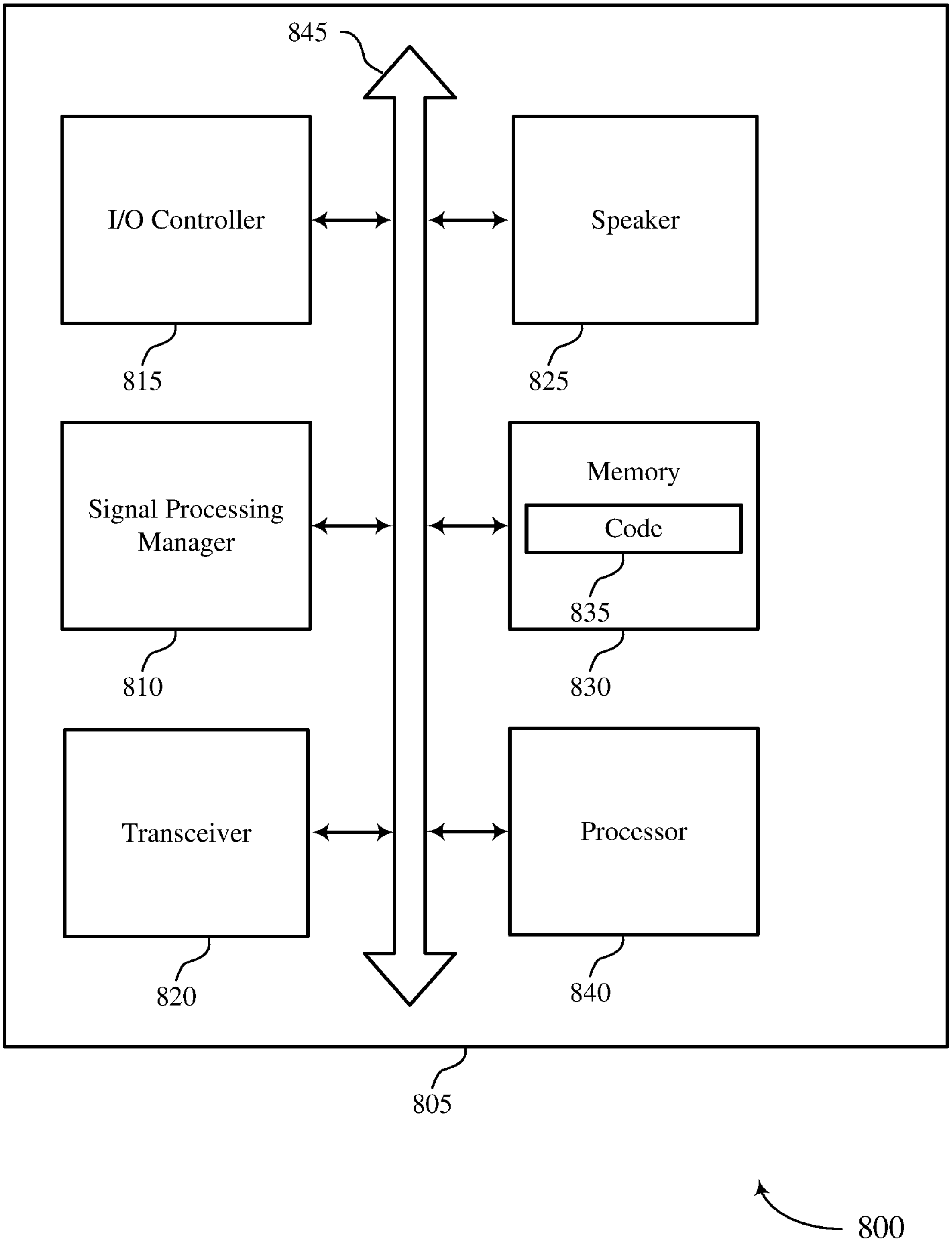
FIG. 8 shows a diagram of a system including a wearable device that supports seamless listen-through for the wearable device in accordance with aspects of the present disclosure.

FIG. 8 shows a diagram of a system 800 including a wearable device 805 that supports seamless listen-through for a wearable device in accordance with aspects of the present disclosure. The wearable device 805 may be an example of or include the components of wearable device 505, wearable device 605, or a wearable device as described herein. The wearable device 805 may include components for bi-directional voice and data communications including components for transmitting and receiving communications, including a signal processing manager 810, an I/O controller 815, a transceiver 820, memory 830, and a processor 840. These components may be in electronic communication via one or more buses (e.g., bus 845).

The signal processing manager 810 may receive, at a wearable device including a set of microphones, an input audio signal, perform, based on the set of microphones, a beamforming operation, isolate, based on the beamforming operation, a self-voice signal and an external signal, apply a first filter to the external signal and a second filter to the self-voice signal, and output, to a speaker of the wearable device, an output audio signal based on a combination of the filtered external signal and the filtered self-voice signal.

The I/O controller 815 may manage input and output signals for the wearable device 805. The I/O controller 815 may also manage peripherals not integrated into the wearable device 805. In some cases, the I/O controller 815 may represent a physical connection or port to an external peripheral. In some cases, the I/O controller 815 may utilize an operating system such as iOS®, ANDROID®, MS-DOS®, MS-WINDOWS®, OS/2®, UNIX®, LINUX®, or another known operating system. In other cases, the I/O controller 815 may represent or interact with a modem, a keyboard, a mouse, a touchscreen, or a similar device. In some cases, the I/O controller 815 may be implemented as part of a processor. In some cases, a user may interact with the wearable device 805 via the I/O controller 815 or via hardware components controlled by the I/O controller 815.

The transceiver 820 may communicate bi-directionally, via one or more antennas, wired, or wireless links. For example, the transceiver 820 may represent a wireless transceiver and may communicate bi-directionally with another wireless transceiver. The transceiver 820 may also include a modem to modulate the packets and provide the modulated packets to the antennas for transmission, and to demodulate packets received from the antennas. In some examples, the listen-through features described above may allow a user to experience natural sounding interactions with an environment while performing wireless communications or receiving data via transceiver 820.

The speaker 825 may provide an output audio signal to a user (e.g., with seamless listen-through features).

The memory 830 may include RAM and ROM. The memory 830 may store computer-readable, computer-executable code 835 including instructions that, when executed, cause the processor to perform various functions described herein. In some cases, the memory 830 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory (e.g., the memory 830) to cause the wearable device 805 to perform various functions (e.g., functions or tasks supporting seamless listen-through for a wearable device).

The code 835 may include instructions to implement aspects of the present disclosure, including instructions to support signal processing. The code 835 may be stored in a non-transitory computer-readable medium such as system memory or other type of memory. In some cases, the code 835 may not be directly executable by the processor 840 but may cause a computer (e.g., when compiled and executed) to perform functions described herein.

Figure 9:
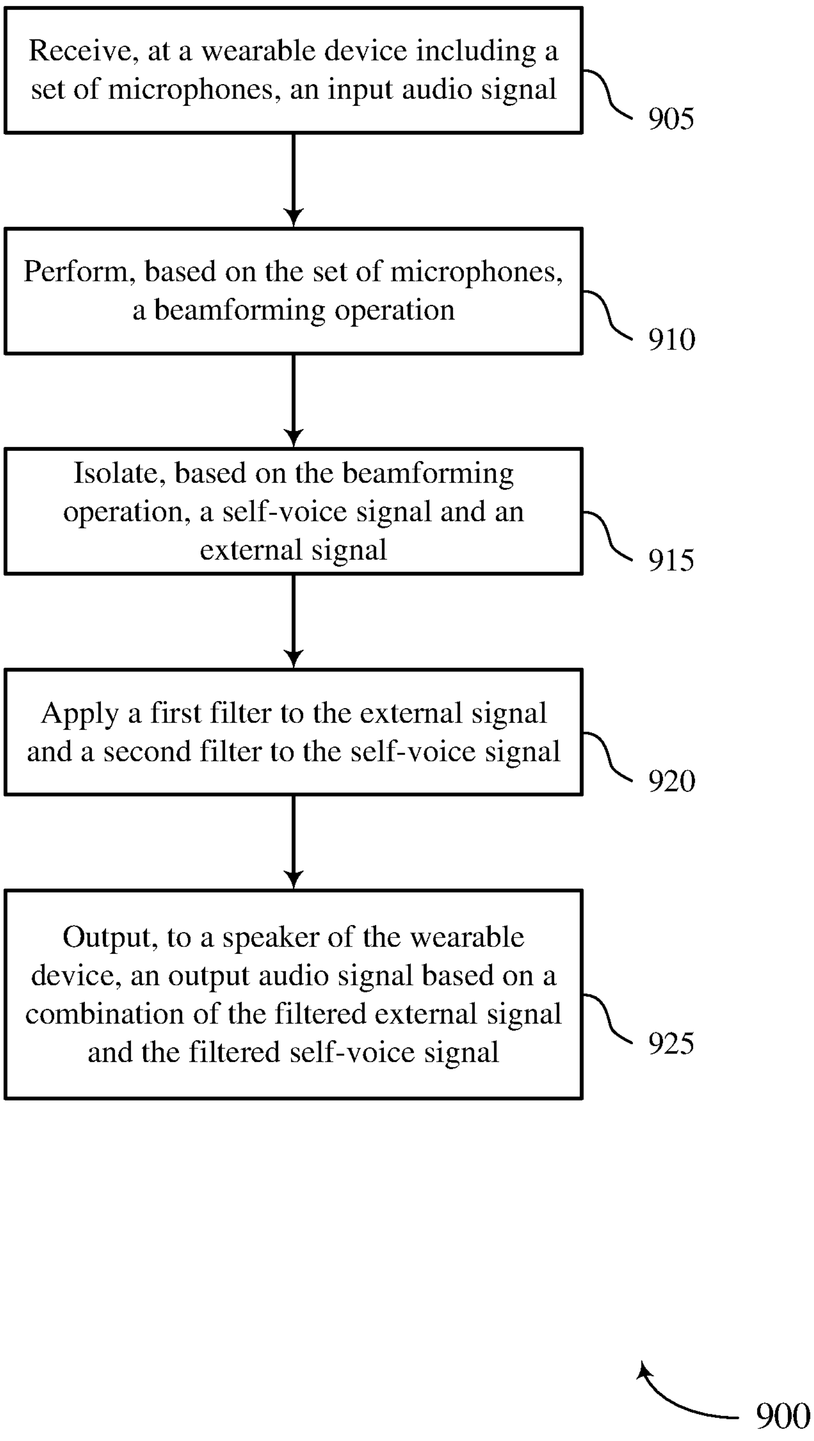
FIGS. 9 and 10 show flowcharts illustrating methods that support seamless listen-through for a wearable device in accordance with aspects of the present disclosure.

FIG. 9 shows a flowchart illustrating a method 900 that supports seamless listen-through for a wearable device in accordance with aspects of the present disclosure. The operations of method 900 may be implemented by a wearable device or its components as described herein. For example, the operations of method 900 may be performed by a signal processing manager as described with reference to FIGS. 5 through 8. In some examples, a wearable device may execute a set of instructions to control the functional elements of the wearable device to perform the functions described below. Additionally, or alternatively, a wearable device may perform aspects of the functions described below using special-purpose hardware.

At 905, the wearable device may receive, at a wearable device including a set of microphones, an input audio signal. The operations of 905 may be performed according to the methods described herein. In some examples, aspects of the operations of 905 may be performed by a microphone manager as described with reference to FIGS. 5 through 8.

At 910, the wearable device may perform, based on the set of microphones, a beamforming operation. The operations of 910 may be performed according to the methods described herein. In some examples, aspects of the operations of 910 may be performed by a beamforming manager as described with reference to FIGS. 5 through 8.

At 915, the wearable device may isolate, based on the beamforming operation, a self-voice signal and an external signal. The operations of 915 may be performed according to the methods described herein. In some examples, aspects of the operations of 915 may be performed by a signal isolation manager as described with reference to FIGS. 5 through 8.

At 920, the wearable device may apply a first filter to the external signal and a second filter to the self-voice signal. The operations of 920 may be performed according to the methods described herein. In some examples, aspects of the operations of 920 may be performed by a filtering manager as described with reference to FIGS. 5 through 8.

At 925, the wearable device may output, to a speaker of the wearable device, an output audio signal based on a combination of the filtered external signal and the filtered self-voice signal. The operations of 925 may be performed according to the methods described herein. In some examples, aspects of the operations of 925 may be performed by a speaker manager as described with reference to FIGS. 5 through 8.

Figure 10:
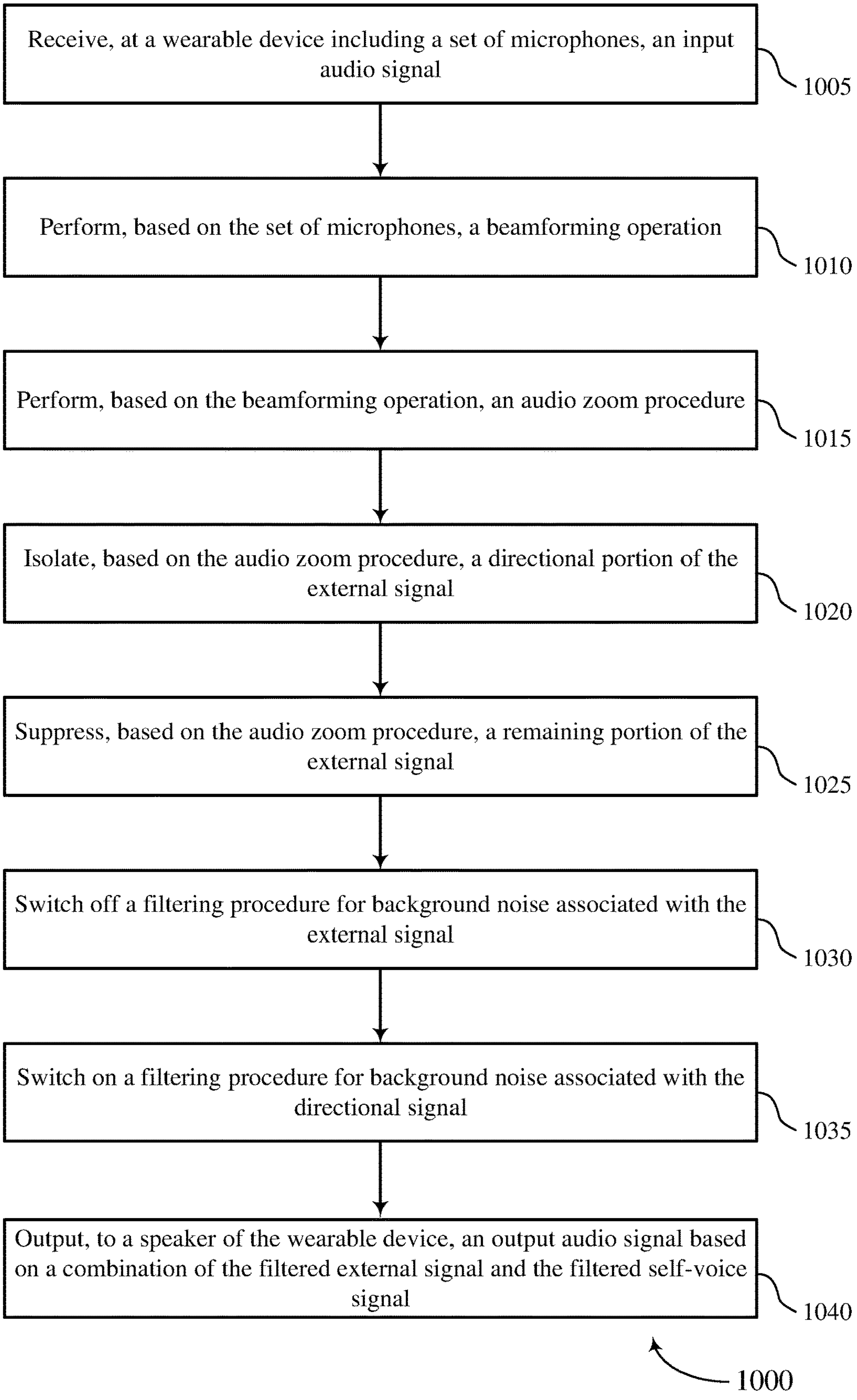

FIG. 10 shows a flowchart illustrating a method 1000 that supports seamless listen-through for a wearable device in accordance with aspects of the present disclosure. The operations of method 1000 may be implemented by a wearable device or its components as described herein. For example, the operations of method 1000 may be performed by a signal processing manager as described with reference to FIGS. 5 through 8. In some examples, a wearable device may execute a set of instructions to control the functional elements of the wearable device to perform the functions described below. Additionally, or alternatively, a wearable device may perform aspects of the functions described below using special-purpose hardware.

At 1005, the wearable device may receive, at a set of microphones, an input audio signal. The operations of 1005 may be performed according to the methods described herein. In some examples, aspects of the operations of 1005 may be performed by a microphone manager as described with reference to FIGS. 5 through 8.

At 1010, the wearable device may perform, based on the set of microphones, a beamforming operation. The operations of 1010 may be performed according to the methods described herein. In some examples, aspects of the operations of 1010 may be performed by a beamforming manager as described with reference to FIGS. 5 through 8.

At 1015, the wearable device may perform, based on the beamforming operation, an audio zoom procedure. The operations of 1015 may be performed according to the methods described herein. In some examples, aspects of the operations of 1015 may be performed by an audio zoom manager as described with reference to FIGS. 5 through 8.

At 1020, the wearable device may isolate, based on the audio zoom procedure, a directional portion of the external signal. The operations of 1020 may be performed according to the methods described herein. In some examples, aspects of the operations of 1020 may be performed by a signal isolation manager as described with reference to FIGS. 5 through 8.

At 25, the wearable device may suppress, based on the audio zoom procedure, a remaining portion of the external signal. The operations of 1025 may be performed according to the methods described herein. In some examples, aspects of the operations of 1025 may be performed by an audio zoom manager as described with reference to FIGS. 5 through 8.

At 1030, the wearable device may switch off a filtering procedure for background noise associated with the external signal. The operations of 1030 may be performed according to the methods described herein. In some examples, aspects of the operations of 1030 may be performed by a filtering manager as described with reference to FIGS. 5 through 8.

At 1035, the wearable device may switch on a filtering procedure for background noise associated with the directional signal. The operations of 1035 may be performed according to the methods described herein. In some examples, aspects of the operations of 1035 may be performed by a filtering manager as described with reference to FIGS. 5 through 8.

At 1040, the wearable device may output, to a speaker, an output audio signal based on a combination of the filtered external signal and the filtered self-voice signal. The operations of 1040 may be performed according to the methods described herein. In some examples, aspects of the operations of 1040 may be performed by a speaker manager as described with reference to FIGS. 5 through 8.

It should be noted that the methods described herein describe possible implementations, and that the operations and the steps may be rearranged or otherwise modified and that other implementations are possible. Further, aspects from two or more of the methods may be combined.

Techniques described herein may be used for various signal processing systems such as code division multiple access (CDMA), time division multiple access (TDMA), frequency division multiple access (FDMA), orthogonal frequency division multiple access (OFDMA), single carrier frequency division multiple access (SC-FDMA), and other systems. A CDMA system may implement a radio technology such as CDMA2000, Universal Terrestrial Radio Access (UTRA), etc. CDMA2000 covers IS-2000, IS-95, and IS-856 standards. IS-2000 Releases may be commonly referred to as CDMA2000 1×, 1×, etc. IS-856 (TIA-856) is commonly referred to as CDMA2000 1×EV-DO, High Rate Packet Data (HRPD), etc. UTRA includes Wideband CDMA (WCDMA) and other variants of CDMA. A TDMA system may implement a radio technology such as Global System for Mobile Communications (GSM).

An OFDMA system may implement a radio technology such as Ultra Mobile Broadband (UMB), Evolved UTRA (E-UTRA), Institute of Electrical and Electronics Engineers (IEEE) 802.11 (Wi-Fi), IEEE 802.16 (WiMAX), IEEE 802.20, Flash-OFDM, etc. UTRA and E-UTRA are part of Universal Mobile Telecommunications System (UMTS). LTE, LTE-A, and LTE-A Pro are releases of UMTS that use E-UTRA. UTRA, E-UTRA, UMTS, LTE, LTE-A, LTE-A Pro, NR, and GSM are described in documents from the organization named "3rd Generation Partnership Project" (3GPP). CDMA2000 and UMB are described in documents from an organization named "3rd Generation Partnership Project 2" (3GPP2). The techniques described herein may be used for the systems and radio technologies mentioned herein as well as other systems and radio technologies. While aspects of an LTE, LTE-A, LTE-A Pro, or NR system may be described for purposes of example, and LTE, LTE-A, LTE-A Pro, or NR terminology may be used in much of the description, the techniques described herein are applicable beyond LTE, LTE-A, LTE-A Pro, or NR applications.

A macro cell generally covers a relatively large geographic area (e.g., several kilometers in radius) and may allow unrestricted access by UEs with service subscriptions with the network provider. A small cell may be associated with a lower-powered base station, as compared with a macro cell, and a small cell may operate in the same or different (e.g., licensed, unlicensed, etc.) frequency bands as macro cells. Small cells may include pico cells, femto cells, and micro cells according to various examples. A pico cell, for example, may cover a small geographic area and may allow unrestricted access by UEs with service subscriptions with the network provider. A femto cell may also cover a small geographic area (e.g., a home) and may provide restricted access by UEs having an association with the femto cell (e.g., UEs in a closed subscriber group (CSG), UEs for users in the home, and the like). An eNB for a macro cell may be referred to as a macro eNB. An eNB for a small cell may be referred to as a small cell eNB, a pico eNB, a femto eNB, or a home eNB. An eNB may support one or multiple (e.g., two, three, four, and the like) cells, and may also support communications using one or multiple component carriers.

The signal processing systems described herein may support synchronous or asynchronous operation. For synchronous operation, the base stations may have similar frame timing, and transmissions from different base stations may be approximately aligned in time. For asynchronous operation, the base stations may have different frame timing, and transmissions from different base stations may not be aligned in time. The techniques described herein may be used for either synchronous or asynchronous operations.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA, or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein can be implemented using software executed by a processor, hardware, firmware, hardwiring, or combinations of any of these. Features implementing functions may also be physically located at various positions, including being distributed such that portions of functions are implemented at different physical locations.

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may include random-access memory (RAM), read-only memory (ROM), electrically erasable programmable ROM (EEPROM), flash memory, compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

As used herein, including in the claims, "or" as used in a list of items (e.g., a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label, or other subsequent reference label.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein

What is claimed is:

1. A wearable device, the wearable device comprising:
- a memory configured to store a self-voice signal via one or more transducers; and
- a processor coupled to the memory, configured to:
  - perform active noise cancelation (ANC) applied to an input audio signal received by at least one microphone;
  - detect the self-voice signal, based on the one or more transducers;
  - apply a first filter to an external audio signal, detected by at least one external microphone on the wearable device, during a listen through operation based on an activation of an audio zoom feature to generate a first listen-through signal that includes the external audio signal;
  - after the activation of the audio zoom feature terminate a second filter that provides low frequency compensation; and
  - produce an output audio signal that is based on at least the first listen-through signal that includes the external audio signal, and is based on the detected self-voice signal.

2. The wearable device of claim 1, wherein the processor is further configured to perform the active noise cancellation (ANC) on at least an internal microphone signal.

3. The wearable device of claim 1, wherein the processor is configured to automatically activate the audio zoom feature based on detection of a condition.

4. The wearable device of claim 1, wherein the condition that the audio zoom feature is triggered is based on voice-detection.

5. The wearable device of claim 1, wherein the processor is configured to perform the ANC and separate the self-voice signal from a background signal in the external audio signal.

6. The wearable deice of claim 5, wherein the self-voice signal is separated from a background signal in the external audio signal based on information from an inner microphone signal detected by an internal microphone of the wearable device.

7. The wearable device of claim 1, wherein the processor is configured to separate the self-voice signal from a background signal in the external audio signal based on using a multi-microphone speech generative network (MSGN).

8. The wearable device of claim 1, wherein the processor is configured to separate the self-voice signal from a background signal in the external audio signal based on using a generalized eigenvalue (GEN) beamforming procedure.

9. The wearable device of claim 1, wherein the one or more transducers includes a bone-conduction sensor, that detects vibrations via bone conduction between a mouth of a user of the wearable device and the one or more transducers.

10. The wearable device of claim 1, wherein the one or more transducers includes at least one inner microphone signals from at least one inner microphone of the wearable device that is configured to detect the at least one inner microphone signal.

11. The wearable device of claim 1, wherein the processor is configured to produce the audio zoom signal of the first listen-through signal based on the activation of the audio zoom feature.

12. The wearable device of claim 11, wherein the processor is configured to produce the audio zoom signal that includes sound of an individual with whom a user wearing the device is conversing.

13. The wearable device of claim 11, wherein the processor is configured to produce the audio zoom signal by suppressing soruces in the external audio signal that do not lie in a targeted direction.

14. The wearable device of claim 11, wherein the processor is configured to produce the audio zoom signal by suppressing the self-voice signal.

15. The wearable device of claim 11, wherein the audio zoom signal provides a stereo sensation in a targeted direction.

16. The wearable device of claim 15, wherein the stereo sensation is produced using a left microphone signal and a right microphone signal.

17. The wearable device of claim 11, wherein the audio zoom signal provides natural sounding listen-through features in a targeted direction.

18. The wearable device of claim 11, wherein the processor is further configured to perform foreground sound processing to produce the audio zoom signal.

19. The wearable device of claim 11, wherein the processor is further configured to perform headphone or earphone equalization to produce the audio zoom signal.

20. The wearable device of claim 1, wherein the device further comprises the at least one external microphone arranged to receive an acoustic signal from an ambient environment, wherein the external audio signal is based on an output of the at least one external microphone.

21. The wearable device of claim 1, wherein the device further comprises at least one internal microphone arranged to receive an acoustic signal from within an ear canal, wherein the internal microphone signal is based on an output of the at least one internal microphone, wherein the at least one internal microphone is one of the one or more transducers.

22. The wearable device of claim 1, wherein the device further comprises a loudspeaker configured to produce a first acoustic signal based on the output audio signal.

23. The wearable device of claim 1, wherein the device further comprises a transceiver, wherein the output audio signal provides natural sounding interactions with an environment while wireless communications is performed or while data is received via the transceiver.

24. The wearable device of claim 1, wherein the termination of the second filter that provides low frequency compensation suppresses the active noise cancellation.

25. The wearable device of claim 1, wherein the audio zoom features enables focus of sound pick up.

26. The wearable device of claim 25, wherein the sound pick up is in a direction.

27. The wearable device of claim 26, wherein the direction is based on beamforming using at least one external microphone on the wearable device and one additional microphone.

28. The wearable device of claim 27, wherein the one additional microphone is an external microphone on the wearable device.

* * * * *